United States Patent
Koziak

(10) Patent No.: US 10,799,550 B2
(45) Date of Patent: Oct. 13, 2020

(54) ORAL COMPOSITIONS COMPRISING BETA-ESCIN FOR REDUCING ACETALDEHYDE TOXICITY

(71) Applicant: ESCILAB SP. Z O.O., Warsaw (PL)

(72) Inventor: Katarzyna Koziak, Warsaw (PL)

(73) Assignee: ESCILAB SP, Z.O.O., Warsaw (PL)

( * ) Notice: Subject to any disclaimer, the term of this patent is extended or adjusted under 35 U.S.C. 154(b) by 0 days.

(21) Appl. No.: 16/461,967

(22) PCT Filed: Nov. 24, 2017

(86) PCT No.: PCT/IB2017/057395
§ 371 (c)(1),
(2) Date: May 17, 2019

(87) PCT Pub. No.: WO2018/096502
PCT Pub. Date: May 31, 2018

(65) Prior Publication Data
US 2019/0321432 A1    Oct. 24, 2019

(30) Foreign Application Priority Data

Nov. 24, 2016 (GB) .................................. 1619846.7

(51) Int. Cl.
| | | |
|---|---|---|
| *A61K 36/00* | (2006.01) | |
| *A61K 36/73* | (2006.01) | |
| *A61P 25/32* | (2006.01) | |
| *A61K 9/00* | (2006.01) | |
| *A61K 31/704* | (2006.01) | |

(52) U.S. Cl.
CPC ............ *A61K 36/73* (2013.01); *A61K 9/0053* (2013.01); *A61K 9/0095* (2013.01); *A61K 31/704* (2013.01); *A61P 25/32* (2018.01)

(58) Field of Classification Search
None
See application file for complete search history.

(56) References Cited

PUBLICATIONS

Balansky, Inhibition of lung tumor development by berry extracts in mice exposed to cigarette smoke: International journal of cancer, (Nov. 1, 2012) vol. 131, No. 9, pp. 1991-7 (Year: 2012).*
Patlolla, beta.-Escin inhibits NNK-induced lung adenocarcinoma and ALDH1A1 and RhoA/Rock expression in A/J mice and growth of H460 human lung cancer cells. Cancer prevention research (Philadelphia, Pa.), (Oct. 2013) vol. 6, No. 10, pp. 1140-9 (Year: 2013).*

* cited by examiner

*Primary Examiner* — Qiuwen Mi
(74) *Attorney, Agent, or Firm* — Servilla Whitney LLC

(57) ABSTRACT

The present invention relates to an oral liquid composition comprising β-escin (beta-escin) and chokeberry fruit extract for use in treatment and prevention of conditions related to the increased acetaldehyde toxicity, such as veisalgia, alcohol poisoning, esophageal cancer, oropharyngolaryngeal cancer or a condition resulting from insufficient aldehyde dehydrogenase (ALDH) enzyme activity. Administration of the composition of the invention to a subject results in an increased metabolism of aldehydic substrates, in particular those originating from catabolism of alcohol and representing a hazard to humans due to their toxicity.

20 Claims, 5 Drawing Sheets

ORAL COMPOSITIONS COMPRISING BETA-ESCIN FOR REDUCING ACETALDEHYDE TOXICITY

CROSS REFERENCE TO RELATED APPLICATIONS

This is a National Phase entry of International Application No. PCT/IB2017/057395, filed Nov. 24, 2017, which claims priority to United Kingdom Patent Application No. 1619846.7, filed Nov. 24, 2016, the disclosures of which are incorporated herein by reference in their entireties.

TECHNICAL FIELD

The present invention relates to an oral liquid composition comprising β-escin (beta-escin) and chokeberry fruit extract for use in treatment and prevention of conditions related to the increased acetaldehyde toxicity, such as veisalgia, alcohol poisoning, esophageal cancer, oropharyngolaryngeal cancer or a condition resulting from insufficient aldehyde dehydrogenase (ALDH) enzyme activity. Administration of the composition of the invention to a subject results in an increased metabolism of aldehydic substrates, in particular those originating from catabolism of alcohol and representing a hazard to humans due to their toxicity. The composition of the invention is also useful in removing aldehydic substrates resulting from metabolism of other xenobiotics, including methanol. As such, the composition of the invention both increases alcohol tolerance and reduces sensitivity to alcohol and is effective in prevention and treatment of veisalgia, in which unpleasant physiological and psychological effects are experienced following the excessive consumption of alcohol.

BACKGROUND ART

Xenobiotics have been defined as chemicals to which an organism is exposed that are extrinsic to the normal metabolism of that organism. Without metabolism, many xenobiotics would reach toxic concentrations. Xenobiotics include pesticides, occupational chemicals, environmental contaminants, clinical drugs, drugs of abuse, deployment-related chemicals, foreign chemicals created by other organisms, etc. Ethyl alcohol (ethanol), also herein referred to as alcohol, is one of the most commonly daily consumed xenobiotics by millions of people worldwide (World Health Organization Global Status Report on Alcohol and Health web page). According to World Health Organization, globally, estimated alcohol consumption in 2016 was 6.4 litres of pure alcohol per person ages 15 or older (World Health Statistics data visualizations dashboard webpage, Harmful use of alcohol).

The consumption of alcoholic beverages, containing ethanol, even in relative moderation, may cause one or more of immediate and delayed alcohol-related effects, which are associated with decreased occupational, cognitive, visual-spatial skill performance, concentration problems and impaired self-regulatory control of behaviour. Continuing normal routine whilst experiencing the effects associated therewith may compromise normal daily activities, such as driving, undertaking labour or operating machinery. Alcohol consumption is a considerable problem since many people will continue with normal activities after said consumption even though their symptoms render normally routine operations dangerous or, at the very least, difficult. The adverse, short and long-term effects of ethanol have been well documented and are linked to its toxicity. Alcohol exerts its effects by altering the function of membrane proteins in many different cell types. Most strongly affected are cells of the gastrointestinal, urinary, cardiovascular, and nervous systems.

Methods to reduce absorption of alcohol following its intake have been for decades a subject of extensive research and at least a few potential solutions could be proposed (see for example *Preventive effect of sesquiterpenes from bay leaf on blood ethanol elevation in ethanol-loaded rat: structure requirement and suppression of gastric emptying*. Matsuda H, Shimoda H, Uemura T, Yoshikawa M., Bioorg Med Chem Lett. 1999 Sep. 20; 9(18):2647-52; *Bioactive saponins and glycosides. VI. Elatosides A and B, potent inhibitors of ethanol absorption, from the bark of Aralia data SEEM. (Araliaceae): the structure-requirement in oleanolic acid glucuronide-saponins for the inhibitory activity*. Yoshikawa M, Murakami T, Harada E, Murakami N, Yamahara J, Matsuda H., Chem Pharm Bull (Tokyo). 1996 October; 44(10):1915-22; *Bioactive saponins and glycosides. III. Horse chestnut. (1): The structures, inhibitory effects on ethanol absorption, and hypoglycemic activity of escins Ia, Ib, IIa, IIb, and IIIa from the seeds of Aesculus hippocastanum L.* Yoshikawa M, Murakami T, Matsuda H, Yamahara J, Murakami N, Kitagawa I., Chem Pharm Bull (Tokyo). 1996 August; 44(8): 1454-64; *E-senegasaponins A and B, Z-senegasaponins A and B, Z-senegins II and III, new type inhibitors of ethanol absorption in rats from senegae radix, the roots of Polygala senega L. var latifolia Torrey et Gray*. Yoshikawa M, Murakami T, Ueno T, Kadoya M, Matsuda H, Yamahara J, Murakami N., Chem Pharm Bull (Tokyo). 1995 February; 43(2):350-2; *Camelliasaponins B1, B2, C1 and C2, new type inhibitors of ethanol absorption in rats from the seeds of Camellia japonica L.* Yoshikawa M, Harada E, Murakami T, Matsuda H, Yamahara J, Murakami N., Chem Pharm Bull (Tokyo). 1994 March; 42(3):742-4). However, it should be noted that adverse effects of alcohol on organs and tissues in humans are only in part related to ethanol, and largely they are a consequence of ethanol metabolism to its primary metabolite acetaldehyde, and associated formation of reactive oxygen and nitrogen species. Alcohol is highly diffusible through cell membranes and is metabolized by most tissues. Thus, the toxicity of its metabolites affects most organs. Importantly, acetaldehyde is also formed from ethanol by microbial alcohol dehydrogenase (see, for example, *High acetaldehyde levels in saliva after ethanol consumption: methodological aspects and pathogenetic implications*. Homann N, Jousimies-Somer H, Jokelainen K, Heine R, Salaspuro M. Carcinogenesis. 1997 September; 18(9):1739-43), which extends the increased exposure to this carcinogen to the whole digestive tract, i.e. where the bacteria of normal human microbiome is found.

Acetaldehyde and oxidants are highly reactive molecules that can damage DNA, proteins and lipids. Changes in hepatic respiration and lipid metabolism lead to tissue hypoxia and impairment in the mitochondrial function. Secondary effects include disruption of signalling pathways and ion channel function, unfolded-protein response and oxidative stress, as well as activation of adaptive immune response largely triggered by acetaldehyde-protein adducts.

Genotoxic and tissue damaging effects and mode of action of acetaldehyde are well described (for example see: *Acetaldehyde* in The MAK-Collection Part I, MAK Value Documentations 2013, Wiley-VCH Verlag GmbH & Co. KGaA). Beyond the health risk in the general population, ~40% of East Asians (~560 million or ~8% of the world's population) carry a mutation that leads to severe accumulation of acetaldehyde. As acetaldehyde is a proven group 1 carcinogen (Baan R, et al.; WHO International Agency for Research on Cancer Monograph Working Group (2007) *Carcinogenicity of alcoholic beverages*. Lancet Oncol 8(4):292-293) and the duration and extent of exposure influences its toxicity, increasing the rate of acetaldehyde clearance may reduce important health risks.

The primary pathway of ethanol involves conversion of ethanol to acetaldehyde by alcohol dehydrogenase (ADH). Acetaldehyde is oxidized further to acetate by aldehyde dehydrogenase (ALDH).

Up to date significant attention has also been paid to means of ameliorating side effects resulting from excessive alcohol consumption. For example, common analgesics, such as aspirin and ibuprofen have been investigated, however no little or no effect on reduction of symptoms was observed. Caffeine, fruits/juices, teas, vitamin lozenges do not appear to provide significant relief of these symptoms and there is no clear evidence to support that any of these provides an improvement in human trials. In addition, many over-the-counter remedies have their own undesirable side effects.

KR20140090453 discloses a hepatoprotective composition for preventing and treatment of hangover comprising a chokeberry fruit extract as an active ingredient. As disclosed therein the alcohol is rapidly decomposed and acetaldehyde, which is generated by the intake of alcohol, is rapidly metabolized, taking advantage of antioxidant activity of the chokeberry fruit extract. However, it is silent about use of any other active ingredients, including saponins.

U.S. Pat. No. 8,137,712 discloses the use of ginseng (some saponin content) in a formulation for the relief of hangover symptoms wherein *Aronia* (chokeberry) may be used as one of a list of colouring agents in a minute amount (0.1% max). However, this publication does not concern formulations devised to include these two specifically selected components in amounts useful to provide a relevant technical effect or that their combination is useful in this regard.

Some saponins extracted from the seeds of *Camellia japonica* L. have been mentioned as a new type inhibitors of ethanol absorption in rats. Nevertheless, this camelliasaponins constitute very specific group of saponins, whose inhibitory effect results from their specific chemical structure. Moreover, the subsequent results of this group presented in publication by M. Yoshikawa et al. in Chem. Pharm. Bull. 42(6) 1357-1359, 1994 identify specific escins (escins-Ia, Ib, IIa, IIb and IIIa) extracted from chestnut tree and their biological activities. In particular, it is stated therein that escins Ia, Ib, IIa and IIb have an inhibitory effect on ethanol absorption in rats that is also related to their chemical structure. However, this publication does also not describe or even suggest escin related effect on ALDH activity in human and animal cells to aid the metabolism of alcohol and thereby reducing the effects associated therewith. Moreover, inhibitory effect on ethanol absorption of saponin was demonstrated in case of oral administration of very high dosages of 200 mg of the saponin fraction of horse chestnut per kg of body weight. In case of the lower dosages, especially in case of dosage amounting 50 mg/kg such inhibitory effect was not so potent.

Even though saponin compositions are known in the prior art, there is no teaching related to effective masking of saponin bitter taste, resulting in a very unpleasant sensation when the saponin containing composition is taken in orally by a subject. Thus, there exist a need for an oral saponin composition, wherein the bitter taste would be well-masked and convenient in oral administration. This problem is evident especially when high doses of saponins are used. Therefore, there exists a need for a composition, wherein the saponin taste is well-masked.

Until now, there have been no evidence or any suggestion that any particular remedies exist that would be simultaneously safe during oral administration for subjects, including humans, and effective for preventing acetaldehyde toxicity resulting in alcohol poisoning or treating veisalgia. Therefore, there still remains a need for a novel composition that is safe, effective and useful as a medicament, particularly for the enhancement of acetaldehyde elimination or the treatment or prevention of veisalgia or other conditions related to the increased acetaldehyde toxicity.

SUMMARY OF THE INVENTION

The subject of invention provides a novel liquid composition for oral administration that enhances metabolism of a toxic acetaldehyde, for example, after excessive consumption of alcohol (ethanol) or in subjects who have an impaired ability to detoxify the given substance. Thus the composition of the invention prevents and treats alcohol poisoning.

Excessive consumption of alcohol is such consumption, which results in veisalgia or even alcohol poisoning symptoms. The amount of alcohol resulting in alcohol poisoning and veisalgia is unique for every subject. The term "alcohol poisoning" as used herein is defined as a condition resulting from consumption of toxic amounts of alcohol, very often manifested by veisalgia symptoms caused by highly toxic aldehydic substrates that originate from catabolism of alcohol.

It is also an object of the invention to provide a novel composition for use as a medicament in the treatment alcohol induced symptoms or treating veisalgia in populations known to be particularly susceptible to a build-up of excess acetaldehyde, such as having a ALDH2*2 genetic mutation.

The present invention relates to a liquid composition for oral administration comprising saponin and chokeberry fruit extract, characterized in that saponin is β-escin, which is present in the composition at a concentration between 20 to 80 mg/l, preferably between 50 mg/l to 75 mg/l, and more preferably β-escin is present at a concentration of 62.5 mg/l, and the chokeberry fruits extract is present in the amount sufficient to mask the taste of β-escin for use in the treatment and/or prevention of metabolic conditions related to the increased acetaldehyde toxicity. In the preferred embodiment the chokeberry fruit extract is present in the composition of the invention at the concentration between 50 to 200 g/l, preferably between 100 g/l to 150 g/l, more preferably between 115 g/l to 135 g/l, and most preferably the chokeberry fruit extract concentration amounts to 125 g/l.

More preferably, the chokeberry fruit extract in the composition of the invention is chokeberry fruit juice concentrate.

In the most preferred embodiment, the composition of the invention comprises β-escin at a concentration of 62.5 mg/l and the chokeberry fruits juice concentrate at the concentration of 125 g/l.

The composition of the invention further comprises a solvent, preferably water or ethanol, and most preferably water.

The composition of the invention is a further preferred embodiment comprises one or more additives selected from flavourings, preservatives, vitamins, sweeteners, anti-foaming agents, antioxidants, $CO_2$ and minerals.

In another embodiment the total volume of the composition of the invention is between 50 ml to 500 ml, preferably between 100 ml to 330 ml, more preferably is between 220 to 300 ml, and most preferably amounts to 275 ml.

The composition of the invention is preferably for use in the treatment of the metabolic condition selected from a group comprising veisalgia, alcohol poisoning esophageal cancer, oropharyngolaryngeal cancer or a condition resulting from insufficient aldehyde dehydrogenase (ALDH) enzyme activity. In preferred embodiment the said condition is in a subject with a genetic mutation ALDH2*2 and more preferably is selected from alcohol-flash reaction and alcohol-induced respiratory reaction.

In a further embodiment a method of treatment and/or prevention of metabolic conditions related to the increased acetaldehyde toxicity resulting from insufficient aldehyde dehydrogenase (ALDH) enzyme activity in a subject is provided, wherein said method comprises oral administration of a liquid composition comprising β-escin and chokeberry fruit extract to the said subject, wherein a concentration of β-escin is between 20 to 80 mg/l and the chokeberry fruits extract is present in the amount sufficient to mask the taste of β-escin. Preferably, the metabolic condition is selected from a group comprising veisalgia, alcohol poisoning, esophageal and oropharyngolaryngeal cancers. Most preferably, the metabolic condition is in a subject with a genetic mutation ALDH2*2.

Since metabolic pathway of other xenobiotics, such as, for example, marihuana, is similar to that of ethanol, the present invention is also useful in ameliorating the effects of such xenobiotics in a subject.

Due to the fact that ALDH oxidizes a wide range of aldehydes, the present invention is also useful in ameliorating the metabolism of toxic aldehydes other than acetaldehyde (see, for example U.S. Pat. No. 9,687,481), such as malondialdehyde (MDA) and 4-hydroxy-2-nonenal (4-HNE), the most mutagenic and the most toxic product of lipid peroxidation, respectively (*Lipid Peroxidation: Production, Metabolism, and Signaling Mechanisms of Malondialdehyde and 4-Hydroxy-2-Nonenal* Ayala A., Muñoz M. F., Argüelles S. Oxidative Medicine and Cellular Longevity, Volume 2014 (2014), Article ID 360438) or a plethora of toxic aldehydes in cigarette smoke and e-cigarette vapors during vaping, including saturated (e.g. formaldehyde, acetaldehyde, 2,3-butanedione, propionaldehyde, butyraldehyde and valeraldehyde) and unsaturated aldehydes (e.g. acrolein, furancarboxaldehyde and crotonaldehyde) (*Critical role of aldehydes in cigarette smoke-induced acute airway inflammation.* Van der Toorn M, Slebos D-J, de Bruin H G, et al. Respiratory Research. 2013; 14(1):45; *E-cigarettes: an evidence update A report commissioned by Public Health England* McNeill A, Brose L S, Calder R, Hitchman S C, Hajek P, McRobbie H, 2015, Public Health England. PHE publications gateway number: 2015260). Importantly, it has been demonstrated that acrolein is an inhibitor of ALDH activity, this mechanism has been link to e.g. lung edema, acute lung injury and endothelial barrier dysfunction and restoring ALDH activity may be z novel approach to prevent and treat acrolein-associated lung diseases, which may occur after smoke inhalation (*Alda-1 Protects Against Acrolein-induced Acute Lung Injury and Endothelial Barrier Dysfunction.* Lu Q, Mundy M, Rounds S, et al. American Journal Of Respiratory Cell And Molecular Biology 2017 August).

As it was already mentioned above, β-escin, like other saponins, has a characteristic bitter taste. Therefore, it results in a very unpleasant sensation when taken in by a subject orally. Surprisingly, the present inventor has found that chokeberry fruit extract has an ability to conceal the taste of β-escin effectively.

BRIEF DESCRIPTION OF DRAWINGS

The subject of the invention was illustrated in a drawing, in which.

DETAILED DESCRIPTION OF THE INVENTION

Figure 1:
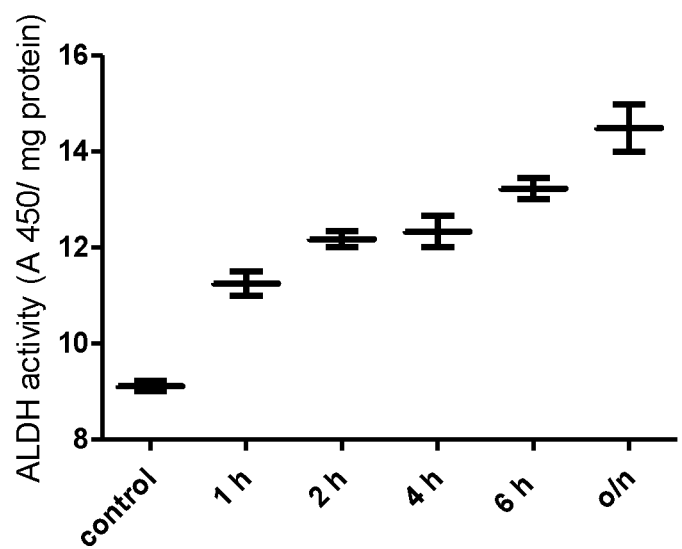
FIG. 1 displays graphically the in-vitro results of β-escin induced aldehyde dehydrogenase (ALDH) activity in human peripheral blood mononuclear cells (PBMC)

Compositions and methods of the invention are useful the prevention and treatment of alcohol-induced symptoms by increasing alcohol tolerance/reducing sensitivity to alcohol. The term "treating" refers to retarding or reversing the progress of, or relieving or alleviating one or more alcohol-induced symptoms. The term "treatment," as used herein, refers to the act of treating one or more alcohol-induced symptoms. The term "preventing" refers to preventing or delaying the onset of one or more alcohol-induced symptoms. The term "prevention," refers to the act of preventing, preventatively treating, or prophylactically treating one or more alcohol-induced symptoms.

β-escin used in a composition of the invention is a mixture of triterpene saponins isolated from horse chestnut seeds (*Aesculus hippocastanum*, L.). Although ethnopharmacological research provides evidence for its broad use to treat numerous diverse disorders, including bladder diseases, cough, diarrhea, dysmenorrhea and tinnitus, its current use is restricted mainly to venotonic and venoprotective indications. Despite the therapeutic significance of β-escin and the popularity of the drug which in the United States and Europe remains one of the best-selling herbal extracts accounting for 226 million U.S. dollar-market in 2014 (IMS Kilochem), its exact mechanism of action remains to be fully elucidated.

β-escin differs from other saponins in chemical structure and activity. For example, it differs from the most commonly investigated camelliasaponins in the length and composition of carbohydrates (i.e. difference in sugar moiety composition). Moreover, the presence of OH group in β-escin triterpene ring in C23 position enables ester formation. This OH group is absent from triterpene ring of camelliasoponin. Further in β-escin OH group in C28 of the triterpene ring can be acetylated, whereas in camelliasaponin OH in the same position is always in non-estrified form. Therefore β-escin and camelliasoponins are both saponins, however they are chemically distinct.

The inventor has observed and confirmed in trials that the composition of the invention has surprising effects in relation to the prevention and treatment of veisalgia, reducing the effects associated with the consumption of alcohol, in particular those associated with toxic aldehydic substrates that originate from alcohol catabolism. Advantageously, the composition permits increased alcohol tolerance and reduces fatigue owing to improved acetaldehyde elimination and reduced ethanol derived oxidative damage.

The inventor has surprisingly found that the composition of the invention induces ALDH activity in human and animal cells to aid the metabolism of alcohol and thereby reducing the effects associated therewith. The invention therefore assists with upregulating the conversion from acetaldehyde to acetate thereby preventing acetaldehyde from either building up or reducing it quickly where there has already been a build-up negating the toxic effects associated with acetaldehyde. High levels of acetaldehyde in the blood can cause adverse reactions including flushing, nausea, and tachycardia. Milder affects manifested as a "hangover" may also include any of the following in combination: headaches, drowsiness, dry mouth, fatigue, sweating, dizziness, nausea, vomiting, anxiety and decreased cognitive or visual-spatial skills. Some effects are thought to result from the fact that acetaldehyde forms adducts with proteins, nucleic acids and other compounds impairing the activity of the affected compounds.

The highest dose of β-escin amounts to 200 mg/l providing to a subject a maximum volume of 500 ml. The relative amount (dose) of β-escin in the composition is significant since this chemical is a potent inhibitor of pancreatic lipase. High dosing can result in steatorrhea or at the very least undesirable abdominal pain. It is therefore important that the dose of this compound is sufficient to achieve the desired technical effect of preventing or reducing alcohol-induced symptoms and/or treating veisalgia without inherently causing unwanted side effects.

The balanced dose of β-escin at the levels according to the invention can provide a useful anti-alcohol poisoning effect without associated unwanted side effects. Moreover combination of β-escin with the chokeberry fruit juice concentrate or chokeberry fruit extracts results in a composition for oral administration wherein the bitter taste of β-escin is very well-masked. Thus the composition has a pleasant taste and can be administered to a subject experiencing gastric symptoms of veisalgia, such as nausea and vomiting.

The composition of the invention comprises chokeberry fruit extract. The term "chokeberry fruit extract" as used herein refers to any liquid formulation obtained from chokeberry fruits, especially chokeberry fruit juice. In the preferred embodiment the composition of the invention comprises a chokeberry fruit juice concentrate. The chokeberry fruit extract, including fruit juice concentrate, may be provided in any form readily known to the skilled person, for example it may be in a dried extract form. Such juice concentrates are readily available commercially and characterised by a Brix value of which extract typically comprise 65-68° Bx. Any suitable alternative supply sufficient to provide the same concentrate of chokeberry concentrate or extract is envisaged.

The combination of components used in the composition of the invention provides enhanced anti-alcohol poisoning effect, at the same time providing appropriate masking of β-escin taste. Under normal conditions (no excess alcohol intake), a balance between reactive oxygen species (ROS) production and antioxidant removal exists in cells. During ethanol oxidation this balance is disrupted and ROS production increases dramatically. The formation of highly reactive oxygen-containing molecules can damage other cell components and therefore is an additional acute consequence which is it desirable to negate. The composition of the invention therefore provides a means to reduce the reactive species by increasing the antioxidant capacity. The studies conducted suggest that the present composition increases the antioxidant capacity of the subject thereby reducing or preventing ethanol derived oxidative damage.

The solvent used in a liquid composition of the invention is preferably water. However, other suitable solvents, such as, for example, ethanol, might also be used. The compositions of the invention may comprise at least about 4% water, at least about 20% water, at least about 40% water, at least about 50% water, at least about 75% water, and at least about 80% water. The water included at these levels includes all added water and any water present in combination components, for example, fruit juice or fruit juice concentrate.

In some embodiments the composition may additionally include one or more additives selected from flavourings, preservatives, vitamins, sweeteners, anti-foaming agents, antioxidants, $CO_2$ and minerals. Some of these additives, such as vitamins, antioxidants and minerals aim to improve well-being of a subject. Other additives, such as flavourings, sweeteners and saturation with $CO_2$ aim to improve taste of the composition of the invention. Finally, additives as anti-foaming agents and preservatives are added to improve composition quality. As β-escin is a surfactant an anti-foaming agents are especially important when the composition of the invention is formulated as a carbonated beverage.

The present invention further extends to a food supplement comprising the above-described compositions.

The oral liquid composition of the invention comprising β-escin, at a concentration of less than 200 mg/l together with chokeberry fruit juice concentrate or extract of 50-200 g/l is disclosed for the first time in use as a medicament. The composition is particularly useful in the treatment of symptoms of excess alcohol consumption and in the treatment of veisalgia.

Where the composition is for use as a medicament, more particularly for in the treatment for treatment of veisalgia it may comprise a single dose or subsequent dosages including the concentration of each active within the definitions above. For example, the composition may comprise a total volume of 275 ml in one single dose, comprising 12.5 mg of β-escin and 25 mg chokeberry fruit juice concentrate.

Preferably the composition is ingested before or during the consuming alcohol. However, it is further demonstrated therapeutic benefit occurs from taking the composition after consumption.

In one further aspect the invention provides a method of treating alcohol poisoning, or a method of preventing the onset of veisalgia symptom, in an individual, comprising administering a composition of the invention. In one embodiment, the administering is prior to, concurrent with, or subsequent to the consumption of alcohol by a subject in the need thereof. The term "subject" as used herein refers to mammals, in particular humans.

Furthermore, there is subset of the population which is believed to particularly benefit from such a composition. It is known that a point mutation (ALDH2*2) in ALDH enzyme family, which is crucial in the pathway processing acetaldehyde, occurs in at least 40% East Asians and 8% of the world population. This subset of the population have a severe deficiency of ALDH 2 and it has been shown that around 20 times more acetaldehyde is found in their blood after consuming alcohol (1-2 units) than those subjects that express normal levels of the same ALDH enzyme. Such a population subgroup has a genetic substitution where the glutamic acid is replaced by lysine at amino acid position 487 of human ALDH2 (to yield mutation E487K). The inactivating mutation is dominant; activity in ALDH2*1/*2 individuals is only 17-30% of the enzyme activity of ALDH2*1/*1 (normal) individuals. This effect has been for example described by David W. Crabb et al. (J Clin Invest. 1989 January; 83(1): 314-316, Genotypes for aldehyde dehydrogenase deficiency and alcohol sensitivity.) in the publication indicating that mitochondrial aldehyde dehydrogenase (ALDH2) activity is responsible for the oxidation of acetaldehyde produced during ethanol metabolism. Individuals with lack of ALDH2 activity, e.g. Asians, suffer the alcohol-flush reaction, caused by acetaldehyde accumulation, when they drink alcoholic beverages. After sequencing the subunit of said homotetrameric enzyme, the abnormality in the inactive enzyme shown to be a substitution of lysine for glutamate at position 487.

Therefore a further aspect the invention provides a composition for use in prevention or treatment of conditions related to the increased acetaldehyde toxicity, such as veisalgia, alcohol poisoning, esophageal cancer, oropharyngolaryngeal cancer or a condition resulting from insufficient aldehyde dehydrogenase (ALDH) enzyme activity in a subject having a point mutation known as ALDH2*2. It is clear that in individuals where one of the key enzyme pathways for processing acetaldehyde is impaired, upregulating the activity of another pathway, such as processing via the enzyme ALDH1 becomes very useful. The mutation does not affect the later pathway and thus it is considered a composition which is shown to increase rates of alcohol catabolism is particularly useful in said individuals.

While performing broad experimental study, including global discovery-type and targeted proteomic methods in conjunction with cellular biology tools to identify novel pathways underlying the protective effects of β-escin in human endothelial cells under inflammatory conditions, the investor has surprisingly found that the drug significantly increases the abundance of cellular ALDH. To further evaluate the observation, the following in vitro and in vivo studies were conducted.

Example 1: Global Proteomic Analysis of Human Endothelial Cells Treated with β-Escin The endothelium is a fundamental functional component of the vasculature, and could be viewed as the largest human endocrine gland/organ, secreting multiple pro/antiangiogenic factors, cytokines and low-molecular-weight mediators controlling the vascular tone. The location of endothelium, at the interface between the circulation and the tissues, makes this epithelial layer particularly exposed to physical and chemical cues coming from the bloodstream. In response to such stimuli, the endothelium modulates its morphology and functions to maintain vascular homeostasis.

Acetaldehyde that is released from the liver travels, reversibly bound, in plasma and erythrocytes and is then taken up by extrahepatic tissues, and in particular by the endothelial cells.

The cellular metabolism of the endothelium is highly dynamic and can quickly adapt to changing environmental conditions. The endothelium indirectly supervises the body's metabolism and is a key intermediate between dietary habits and health consequences. It has been demonstrated that due to its wide distribution throughout the body, vascular endothelium is involved i.a. in the extrahepatic metabolism of acetaldehyde significantly contributing to its degradation (*Metabolism of acetaldehyde by rat isolated aortic rings: Does endothelial tissue contribute to its extrahepatic metabolism?* Tampier L., Cariz S., Quintanilla M E. Alcohol, 1993, May-June, 10 (3): 203-206). Importantly, it is generally accepted that acetaldehyde exerts a potent vascular effect, for example by its depressant action on vascular smooth muscle and induced vasodilation. It has been also well documented that it is the blood acetaldehyde, and not blood ethanol that underlie the pathogenesis of the alcohol flush (*Alcohol ingestion and the cutaneous vasculature* Wolf R., Tüzün B., Tüzün Y. Clinics in Dermatology, 1999, July-August, 17 (4): 395-403). Therefore, an increase in acetaldehyde degradation by endothelial cells could directly affect the rate of its clearance.

To investigate the effect of β-escin on endothelial aldehyde dehydrogenases, including the novel alcohol-metabolizing members of this family (ALDH1L1, ALDH1L2, ALDH1A2, ALDH3B1, ALDH5A1, ALDH6A1, and ALDH18A1) which were attained through the genome-wide component study (*Associations and interactions between SNPs in the alcohol metabolizing genes and alcoholism phenotypes in European Americans* Sherva R. et al. Alcoholism, Clinical and Experimental Research, 2009 May, 33(5): 848-857), the inventor performed global discovery-type proteomic analysis of human endothelial cells response to β-escin treatment.

Extensive research clearly supports the idea that dietary components can significantly affect endothelial function.

Human Umbilical Vein Endothelial Cells (HUVEC, sex unknown, Lonza) were cultured in the EBM-2 (Lonza) supplemented with endothelial growth supplement mix (EGM-2 SingleQuot Kit Supplements and Growth Factors, Lonza) under standard cell culture condition (37° C., 5% CO2). Cells were harvested using Accutase (PAA Laboratories). The experiments were performed with cells of passage four. The cells were treated for 24 h with DMSO-solubilized 3 µM β-escin (Nobilus Ent). As DMSO concentration in cell culture media did not exceed 0.015%, i.e. its effect of HUVEC was negligible (*Comparison of PrestoBlue and MTT assays of cellular viability in the assessment of anti proliferative effects of plant extracts on human endothelial cells* Bonder M, Rozalski M, Krajewska U, Podsedek A, Watala C. Journal of pharmacological and toxicological methods. 2014; 69(1): 9-16) DMSO controls were not included in the experimental protocols. Detailed description of sample preparation for Isobaric Tags for Relative and Absolute Quantitation (iTRAQ) analysis and global proteomic analysis of cells treated with β-escin are presented in Domanski et al. (*Molecular mechanism for cellular response to β-escin and its therapeutic implications* Domanski D, Zegrocka-Stendel O, Perzanowska A, Dutkiewicz M, Kowalewska M, Grabowska I, Maciejko D, Fogtman A, Dadlez M, Koziak K. PLoS One. 11, e0164365, 2016). Briefly, the discovery-type proteomic analysis was carried out using the Isobaric Tags for Relative and Absolute Quantitation (iTRAQ) method which enables the identification and relative quantitation of all detectable proteins present in the samples. Proteins were identified with Mascot and differentially expressed proteins were assessed using the Diffprot and MScan software tools with estimation of statistical significance. A minimum number of two peptides with a false-discovery rate<1% were used for confident identification of a protein in the iTRAQ experiment. Proteins with a q-value lower than 0.05 and a fold-change higher than 1.1 were considered as significantly differentially expressed and whose change in relative abundance is relevant.

Differential proteome analysis of the β-escin-treated endothelial cells using iTRAQ revealed that β-escin significantly increased the abundance of at least two enzymes involved in alcohol metabolism and affecting human sensitivity to metabolic disorders related to acetaldehyde accumulation: aldehyde dehydrogenase 18 family member A1 (ALDH18A1, accession number P54886, q-value 0.00644, fold-change 1.1) and aldehyde dehydrogenase 1 family member A1 (ALDH1A1, accession number P00352, q-value 0.0078, fold-change 1.1). The observed change in the amounts of other ALDH family members following β-escin treatment, i.e. ALDH6A1, ALDH1A2, ALDH9A1, ALDH1B1, ALDH4A1, ALDH16A1, ALDH2 and ALDH7A1 did not reach statistical significance in this analysis.

Example 2: ALDH Activity In Vitro

Following differential proteome analysis of the β-escin-treated endothelial cells using iTRAQ which discovered significant changes in the protein expression profile (i.e. protein content) of ALDH family members, the inventor performed functional analysis of ALDH (i.e. its enzymatic activity) to further investigate the observed phenomena.

ALDH activity was evaluated in human peripheral blood mononuclear cells (PBMC) obtained from healthy blood donors and in mouse muscle cells (C2C12).

Peripheral blood mononuclear cells (PBMC) have been isolated from healthy male donors under standard protocol regarding density gradient centrifugation. In brief, 30 ml of twice diluted blood has been layered on 15 ml of Lymphoprep (Axis-shield) and centrifuged at 800×g for 15 minutes. The layer of PBMC has been collected, the cells have been washed twice in phosphate buffered saline (PBS) (BIOMED-LUBLIN, Poland) and suspended in RPMI 1640 medium (Gibco), containing 10 mM HEPES (Sigma), 10% fetal calf serum (BIOMED-LUBLIN) and antibiotic-antimycotic solution (streptomycin sulfate, sodium penicilate G, amphotericin B, PAA, Austria).

Enzymatic activity of ALDH was assessed with Aldehyde Dehydrogenase Activity Colorimetric Assay Kit (Sigma Aldrich) according to manufacturer's instructions. In this test ALDH activity is determined by a coupled enzyme assay in which acetaldehyde is oxidized by ALDH generating NADH, which reacts with a probe generating a colorimetric (450 nm) product proportional to the ALDH activity present.

Figure 2:
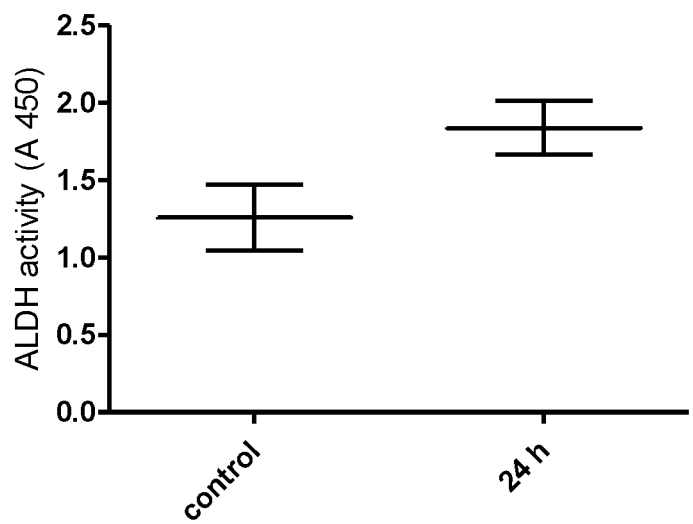
FIG. 2 displays graphically the in-vitro results of β-escin induced ALDH activity in mouse muscle cells (C2C12)

As shown in FIGS. 1 and 2, β-escin causes a potent increase in ALDH activity in both cell types.

Figure 3:
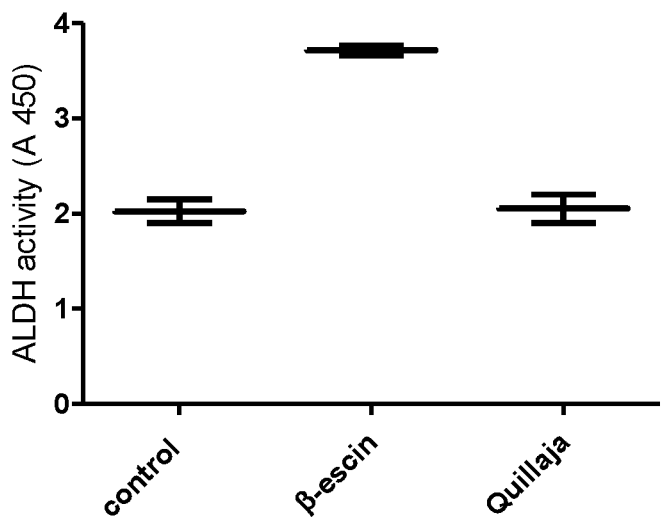
FIG. 3 shows the ALDH activity in mouse muscle cells (C2C12) following the in-vitro treatment with β-escin and *Quillaja saponaria* saponin.

To test the specificity of the β-escin effect on ALDH activity, the inventor investigated the results of cellular treatment with saponin extracted from the soap bark tree *Quillaja saponaria*. The results presented in FIG. 3 depict timeline of ALDH activity in C2C12 mouse muscle cell line following the overnight (o/n) treatment with β-escin (20 μM) and *Quillaja saponaria* saponin (20 μM) and clearly show that *Quillaja saponaria* saponin does not induce ALDH activity. From this analysis, it can be concluded that not all saponins have the same effect on ALDH activity. Thus not all saponins are effective in treatment or prevention of conditions caused by aldehydic substrates originating from catabolism of alcohol.

Figure 4:
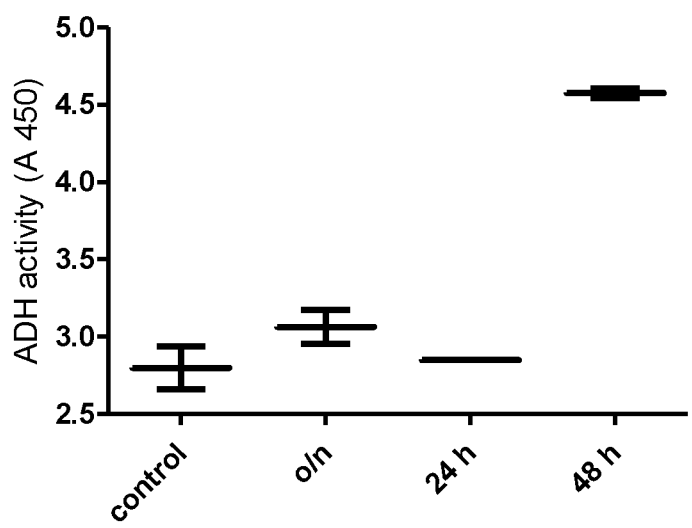
FIG. 4 displays graphically the in-vitro results of β-escin induced alcohol dehydrogenase (ADH) activity in mouse muscle cells (C2C12)

In parallel to ALDH activity assessment, the inventor assayed the influence of β-escin on alcohol dehydrogenase (ADH) activity using the Alcohol Dehydrogenase Activity Assay kit (Sigma Aldrich). In the assay ADH activity is determined using isopropanol as the substrate in an enzyme reaction, which results in a colorimetric (450 nm) product proportional to the enzymatic activity present. As shown in FIG. 4, β-escin did not influence ADH activity in timeline corresponding to ALDH response and an increase in ADH activity was detected only after 48 hour-treatment Example 3: Formulation Taste Assays β-escin is characterized by a particularly strong bitterness. Blocking the unpleasant bitter taste in the assayed formulation presented a challenge, which had to be overcome to obtain its beneficial health effects. One of the aims of the invention was to provide compositions, in which the bitter taste of β-escin would be concealed.

Particularly good taste masking properties were obtained with chokeberry fruit juice concentrate permitting to provide as much as 30 mg of β-escin in one dose of 275 ml (higher doses of β-escin were not tested due to the increased risk of steatorrhea and abdominal pain). In the studies liquid oral compositions containing 5; 7.5; 10; 12.5; 15; 17.5; 20; 22.5; 25; 27.5 and 30 mg of β-escin and 25 g of chokeberry fruit juice concentrate in water in a total volume of 275 ml were administered to 10 subjects. Majority of subjects indicated 17 mg as the maximum taste-comfortable dose in a single dose of 275 ml; then, with the increase of β-escin content, the perception of taste decreased. The chokeberry (*Aronia melanocarpa*) content provides considerable advantage also due to its one of the highest antioxidant activities among fruits. Its role in the prevention and treatment of oxidative stress-related diseases has been solidly documented. It is evident that antioxidant effects of chokeberry extends far beyond radical scavenging and includes suppression of reactive oxygen and nitrogen species formation, inhibition of prooxidant enzymes, restoration of antioxidant enzymes, and cellular signaling to regulate the level of antioxidant compounds and enzymes (*Bioavailability and Antioxidant Activity of Black Chokeberry (Aronia melanocarpa) Polyphenols: in vitro and in vivo Evidences and Possible Mechanisms of Action: A Review*. Denev, P. N., Kratchanov, C. G., Ciz, M., Lojek, A., Kratchanova, M. G. Comprehensive Reviews in Food Science and Food Safety, 2012 August; 11(5): 471-489).

Other fruit juice was less effective in masking β-escin taste, as shown by a study carried out in an analogous manner to the study described above for chokeberry fruit juice. For example, for apple juice the maximum dose of β-escin acceptable by the subject was as low as 4 mg and was not improved with the addition of sweeteners, such as Steviose.

Example 4: In-Vivo Studies

1. Study No 1

A 50 year old, healthy male volunteer fasted for 12 hours before commencing a 3 day study in which on each of day 0, day 1 and day 2, 40 g of ethanol was ingested. On day 0 no composition was tested providing a base control for its activity. On day 1, one hour prior to alcohol intake, the subject was given a 200 ml beverage comprising 12.5 mg β-escin and 25 g chokeberry fruit juice concentrate to consume. On day 2, one hour prior to alcohol intake, the subject was given a 200 ml beverage comprising 12.5 mg β3-escin and 25 g chokeberry fruit juice concentrate to consume.

Figure 5:
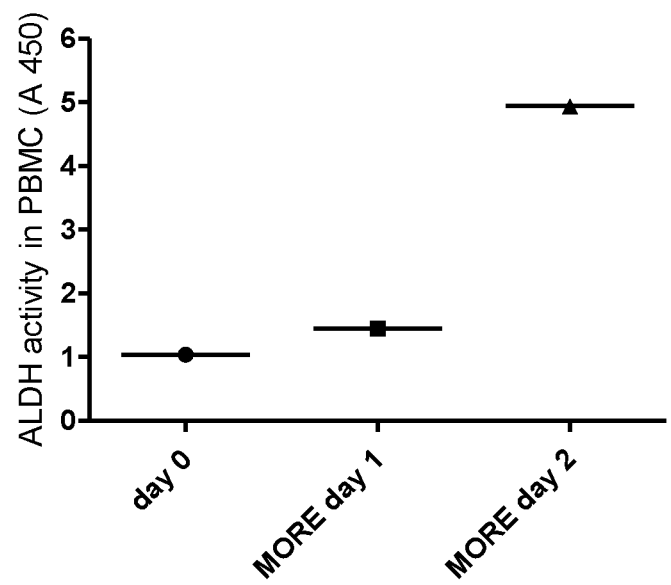
FIG. 5 displays graphically the in-vivo results of β-escin effect on ALDH activity in PBMC obtained from the subject.
Figure 6:
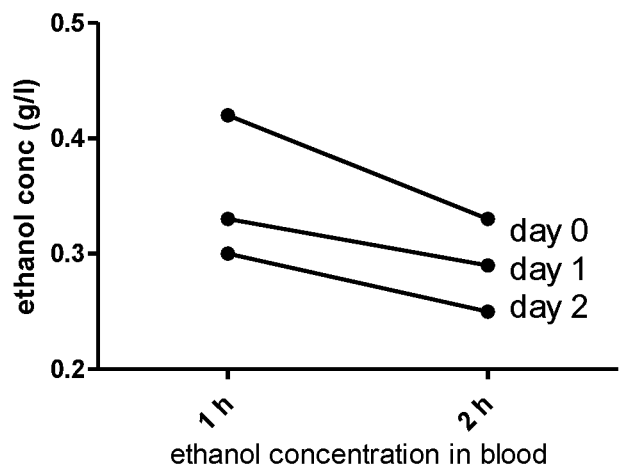
FIG. 6 displays graphically the in-vivo results of β-escin effect on ethanol concentration in blood.
Figure 7:
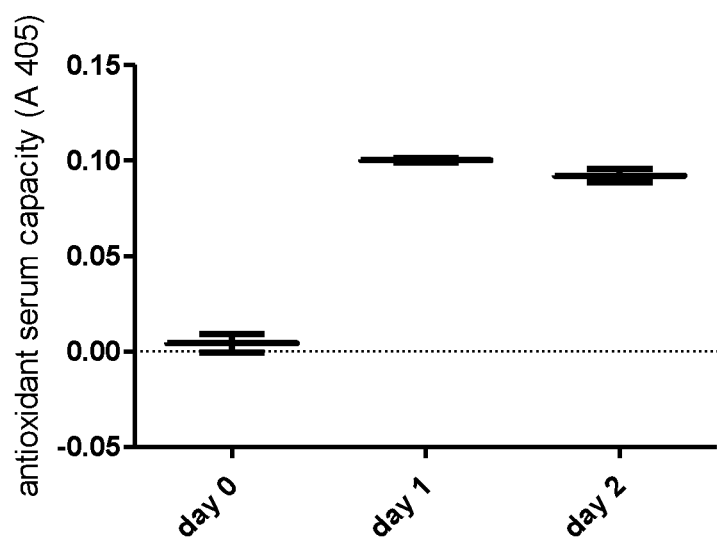
FIG. 7 shows in vivo results of the antioxidant capacity of the subject's serum.

Blood samples were obtained 1 and 2 hours after the alcohol (ethanol) consumption and a biochemical analysis of the blood was undertaken. The results presented in FIGS. 5, 6 and 7 depict the in vivo effects resulting from the β-escin and chokeberry-containing composition, namely: the ALDH activity in PBMC; the effect on ethanol concentration in blood; and the antioxidant capacity of the subject's serum, respectively.

Peripheral blood mononuclear cells (PBMC) have been isolated from the subject as described above in the in vitro studies examples.

Enzymatic activity of ALDH in PBMC was assessed with Aldehyde Dehydrogenase Activity Colorimetric Assay Kit (Sigma Aldrich) as described above for the in vitro studies. Antioxidant capacity of the serum was measured with Antioxidant Assay Kit (Sigma Aldrich) strictly following the manufacturer's instructions. The antioxidant assay is based on the formation of a ferryl myoglobin radical from myoglobin and hydrogen peroxide, which oxidizes the ABTS (2,2'-azino-bis(3-ethylbenzthiazoline-6-sulfonic acid)) to produce a radical cation ABTS+, a soluble green color chromogen that can be determined at 405 nm. In the presence of antioxidants the radical cation is suppressed to an extent dependent on the activity of the antioxidant and the color intensity is decreased proportionally. Trolox, a water-soluble vitamin E analogue, serves as a standard or a control antioxidant.

As shown in the graph (FIG. 5), the ALDH enzyme activity level increases dramatically from day 0 to day 1 and to day 2 following an intake of the tested beverage. The graph depicts the change in ALDH activity presented as a percentage of values obtained on day 0. The increase in ALDH activity was significant already on day 1 reaching 160% and even more enhanced on day 2 with the value of 437%. Concomitantly, the rise in the serum antioxidant capacity is observed. Importantly, the serum antioxidant potential achieved with the tested beverage is not lessened with alcohol consumed by the subject.

2. Study No 2

A 50 year old, healthy male volunteer fasted for 12 hours before commencing a 3 day study in which on each of day 0, day 1 and day 2, he ingested 40 g of ethanol. On day 0 no composition was tested providing a base control for its activity. On day 1, 15 minutes after alcohol consumption the subject was given 200 ml beverage comprising 12.5 mg β-escin and 25 g chokeberry fruit juice concentrate to consume. On day 2, 15 minutes after alcohol consumption the subject was given a 200 ml beverage comprising 12.5 mg β-escin and 25 g chokeberry fruit juice concentrate to consume.

Blood samples were obtained 1 and 2 hours after the alcohol (ethanol) consumption for ethanol concentration measurement.

Ethanol concentration in blood was measured in Analyzer Dimension (Siemens) with the use of Reagent Dimension® Flex® Quantitative Measurement Ethyl Alcohol. The ETOH method is an in vitro diagnostic test for the quantitative measurement of ethyl alcohol (ethanol) in human serum, plasma, and urine on the Dimension® clinical chemistry system. Ethyl alcohol test results may be used in the diagnosis and monitoring of ethyl alcohol intoxication and poisoning.

Figure 8:
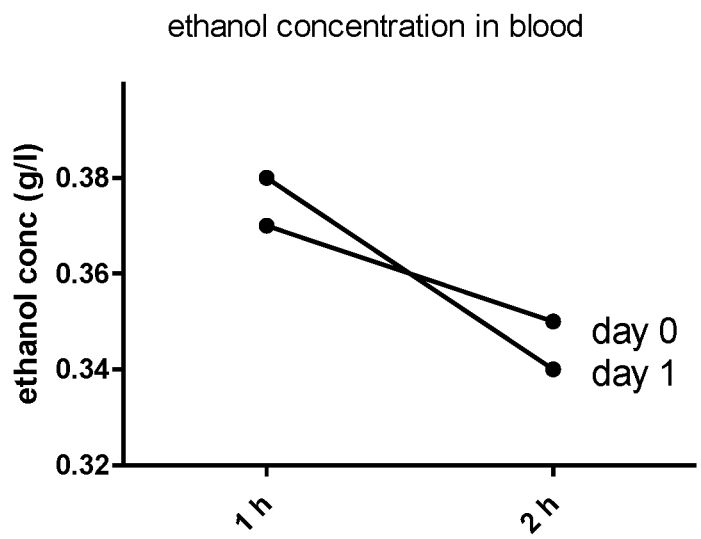
FIGS. 8 and 9 show the in-vivo results of β-escin effect on ethanol concentration in blood when the composition of the invention is ingested post-alcohol consumption.
Figure 9:
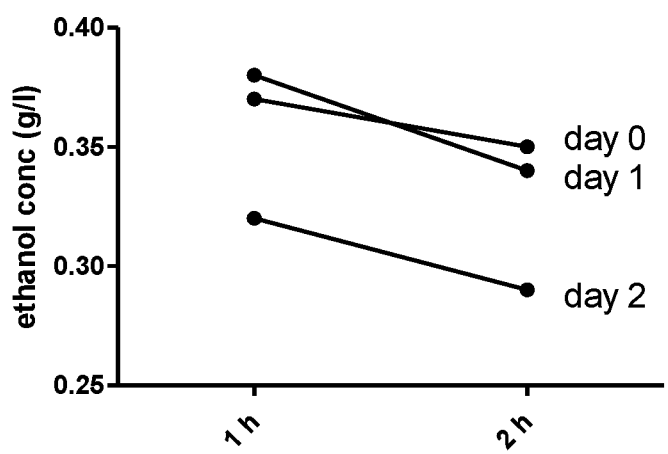

The results presented in FIGS. 8 and 9 depict the in vivo effects resulting from the β-escin and chokeberry-containing composition, namely: the effect on ethanol concentration in blood.

The graph in FIG. 8 presenting ethanol clearance from blood indicates a significant change in the elimination curve between day 0 and day 1. It shows that the β-escin and chokeberry-containing beverage affects the kinetics of this process also when it is consumed after alcohol.

On day 2, as shown in FIG. 9, the anti-alcohol poisoning effect is even more evident, reflecting combined effects of consecutive day's consumption of the composition of the invention. The ethanol lowering effect observed clearly on day 2 is most probably related to the increased ADH activity which is evoked with β-escin only after 48 hours.

The theoretical basis together with the in-vitro and human studies carried out by the inventor demonstrate a sound basis that the composition of the invention provides useful technical effects when administered to subjects, especially humans. The compositions can be used on a regular basis, for example once a day, providing a continuous effect and are therefore useful as medicaments, particularly useful in the prevention and/or treatment of alcohol-induced acetaldehyde toxicity and veisalgia symptoms.

The invention claimed is:

1. A liquid composition for oral administration comprising saponin and chokeberry fruit extract, characterized in that saponin is β-escin, which is present in the composition at a concentration between 20 to 80 mg/l and the chokeberry fruits extract is present in the amount sufficient to mask the taste of β-escin for use in the treatment and/or prevention of metabolic conditions related to the increased acetaldehyde toxicity.

2. The composition of claim 1, wherein the concentration of β-escin is between 50 mg/l to 75 mg/l.

3. The composition of claim 2, wherein the concentration of β-escin is 62.5 mg/l.

4. The composition of claim 1, wherein the chokeberry fruit extract is present in the composition at the concentration between 50 to 200 g/l.

5. The composition of claim 4, wherein chokeberry fruit extract is present in the composition at the concentration between 100 g/l to 150 g/l.

6. The composition of claim 5, wherein chokeberry fruit extract is present in the composition at the concentration between 115 g/l to 135 g/l.

7. The composition of claim 6, wherein chokeberry fruit extract is present in the composition at the concentration of 125 g/l.

8. The composition of claim 1, wherein chokeberry fruit extract is chokeberry fruit juice concentrate.

9. The composition of claim 8, wherein β-escin is present at a concentration of 62.5 mg/l and the chokeberry fruit juice concentrate is present at the concentration of 125 g/l.

10. The composition of claim 1, further comprising a solvent.

11. The composition of claim 10, wherein the solvent is water or ethanol.

12. The composition of claim 1, further comprising one or more additives selected from the group consisting of flavourings, preservatives, vitamins, sweeteners, anti-foaming agents, antioxidants, $CO_2$ and minerals.

13. The composition of claim 1, wherein the total volume of the composition is between 50 ml to 500 ml.

14. The composition of claim 13, wherein the total volume of the composition is between 100 ml to 330 ml.

15. The composition of claim 14, wherein the total volume of the composition is between 220 to 300 ml.

16. The composition of claim 15, wherein the total volume of the composition is 275 ml.

17. The composition of claim 1, wherein the metabolic condition is selected from the group consisting of veisalgia, alcohol poisoning esophageal cancer, oropharyngolaryngeal cancer and a condition resulting from insufficient aldehyde dehydrogenase (ALDH) enzyme activity.

18. The composition of claim 17, wherein the metabolic condition is a condition resulting from insufficient aldehyde dehydrogenase (ALDH) enzyme activity and a subject has a genetic mutation ALDH2*2.

19. A method of treatment and/or prevention of metabolic conditions related to the increased acetaldehyde toxicity resulting from insufficient aldehyde dehydrogenase (ALDH) enzyme activity in a subject comprising oral administration a liquid composition comprising β-escin and chokeberry fruit extract to the said subject, wherein a concentration of β-escin is between 20 to 80 mg/l and the chokeberry fruits extract is present in the amount sufficient to mask the taste of β-escin.

20. The method of claim 19, wherein the metabolic condition is selected from the group consisting of veisalgia, alcohol poisoning esophageal and oropharyngolaryngeal cancers.

* * * * *